US008084755B2

(12) United States Patent
Hall et al.

(10) Patent No.: US 8,084,755 B2
(45) Date of Patent: Dec. 27, 2011

(54) TIME-DOMAIN METHOD AND APPARATUS FOR DETERMINING THE DEPTH AND CONCENTRATION OF A FLUOROPHORE IN A TURBID MEDIUM

(75) Inventors: David Jonathan Hall, San Diego, CA (US); Guobin Ma, Dorval (CA); Frederic Lesage, Montreal (CA); Pascal Gallant, Laval (CA)

(73) Assignee: Softscan Healthcare Group Ltd., Tortola (VG)

( * ) Notice: Subject to any disclaimer, the term of this patent is extended or adjusted under 35 U.S.C. 154(b) by 0 days.

(21) Appl. No.: 13/023,851

(22) Filed: Feb. 9, 2011

(65) Prior Publication Data

US 2011/0133064 A1 Jun. 9, 2011

Related U.S. Application Data

(62) Division of application No. 10/577,527, filed as application No. PCT/IB2004/003559 on Oct. 29, 2004, now Pat. No. 7,960,707.

(60) Provisional application No. 60/515,697, filed on Oct. 31, 2003.

(51) Int. Cl.
*G01J 1/58* (2006.01)
*G21H 3/02* (2006.01)
*G01N 21/64* (2006.01)

(52) U.S. Cl. ........... 250/459.1; 250/461.2; 250/252.1; 356/317; 356/417

(58) Field of Classification Search .......... 250/459.1, 250/461.2, 252.1; 356/317, 417; 600/407, 600/300

See application file for complete search history.

(56) References Cited

U.S. PATENT DOCUMENTS

| 4,135,816 | A | | 1/1979 | Niemann et al. |
| 5,650,135 | A | | 7/1997 | Contag et al. |
| 5,814,820 | A | * | 9/1998 | Dong et al. ............... 250/458.1 |
| 6,280,378 | B1 | * | 8/2001 | Kazuhiro et al. ........... 600/160 |
| 6,321,111 | B1 | | 11/2001 | Perelman et al. |

(Continued)

FOREIGN PATENT DOCUMENTS

WO 02/093143 11/2002

OTHER PUBLICATIONS

Haiyong, Quan et al., Institute of Electrical and Electronics Engineers, "A New 3D Fluorescence Imaging Method", Proceedings of the IEEE 29th Annual Northeast Bioengineering Conference, Newark, Nj Mar. 22-23, 2003, Proceedings of the IEEE Annual Northeast Bioengineering Conference, New York, NY IEEE, US, Vol. Conf. 29, Mar. 22, 2003, pp. 333-334.

*Primary Examiner* — David Porta
*Assistant Examiner* — Jessica L Eley
(74) *Attorney, Agent, or Firm* — Day Pitney LLP

(57) ABSTRACT

Methods and apparatuses for determining the depth and concentration of fluorophores in a turbid medium are disclosed. The method advantageously provides for a rapid estimation of the depth of the flurophore using characteristics of a temporal point spread function. The concentration of the fluorophore can be determined using the method of the present invention by combining a calculated depth of the flurophore with a measurement of the intensity of the emitted fluorescence. The intensity can be accurately measured by the apparatus disclosed herein which combine back-reflection and trans-illumination geometries for the source of light injecting and detection.

28 Claims, 6 Drawing Sheets

U.S. PATENT DOCUMENTS

| | | |
|---|---|---|
| 6,615,063 B1 | 9/2003 | Ntziachristos et al. |
| 6,775,567 B2 | 8/2004 | Cable et al. |
| 2002/0064789 A1 * | 5/2002 | Weiss et al. .................. 435/6 |
| 2003/0123058 A1 | 7/2003 | Luryi et al. |
| 2008/0312879 A1 | 12/2008 | Fortier et al. |
| 2009/0216457 A1 | 8/2009 | Ma |

* cited by examiner

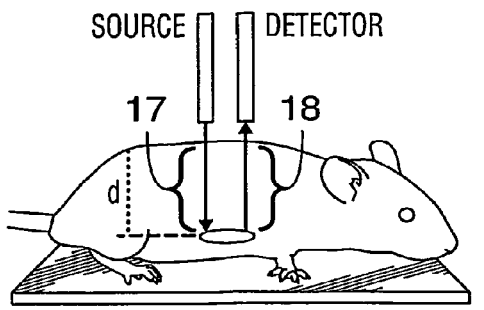
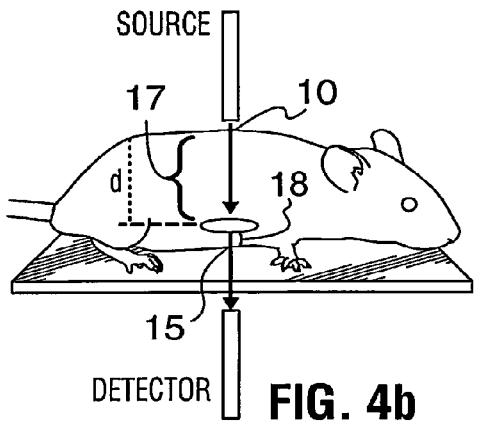
FIG. 4a  FIG. 4b
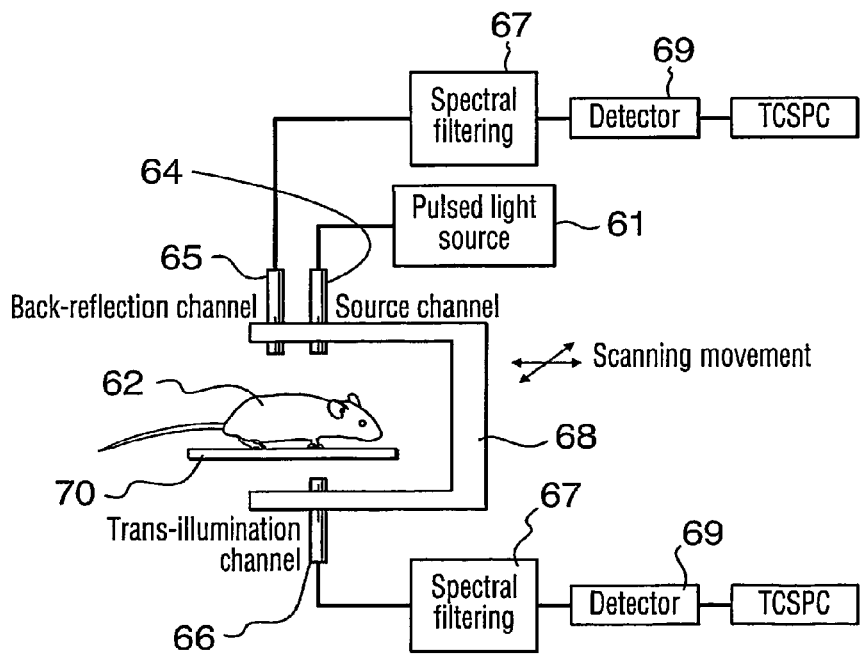
FIG. 6

TIME-DOMAIN METHOD AND APPARATUS FOR DETERMINING THE DEPTH AND CONCENTRATION OF A FLUOROPHORE IN A TURBID MEDIUM

CROSS-REFERENCE TO RELATED APPLICATIONS

This application is a divisional of U.S. Ser. No. 10/577,527, filed on Mar. 12, 2007, which is a §371 national stage filing of International Application No.: PCT/IB2004/003559 filed on Oct. 29, 2004, which claims priority to U.S. Provisional Application No. 60/515,697 filed on Oct. 31, 2003.

TECHNICAL FIELD

This application relates to fluorescence measurements in turbid media.

BACKGROUND OF THE INVENTION

The use of fluorophores for identifying or localizing structures within objects is of considerable importance in diverse fields and in biological/medical applications in particular. Optical fluorescence imaging of turbid media such as biological tissue, is primarily achieved with Continuous Wave (CW) methods. Typically a light source is employed to illuminate the object of interest, e.g. a mouse in vivo, and the emitted CW fluorescence intensity signal from the flurophore is measured directly with a camera. Systems in which the fluorescence from small animals comprising bioluminescent molecules can be measured have been described. See for example, U.S. Pat. Nos. 6,775,567 and 5,650,135.

For applications such as diagnosis and pharmacological studies, it is often desirable to determine the concentration and depth of the fluorophore. However, to assume that the direct CW fluorescence intensity signal is proportional to the flurophore concentration can be misleading since the depth of the flurophore will also impact the CW fluorescence intensity signal. In fact, given a single CW source and CW detector measurement it is impossible to decouple flurophore concentration and depth.

To address this problem of decoupling depth and concentration in CW measurements, some researchers are exploring CW tomography, in order to reconstruct a three-dimensional distribution of the flurophore concentration in the object, thereby attempting to account for the depth of the fluorophore. However, these tomographic approaches require multiple source-detector pair measurements from many angles, combined with complex, computer intensive inversion algorithms. Furthermore, CW tomography requires an assumption about the scattering coefficient of the object, since CW can neither decouple the intrinsic absorption and scattering of the object.

The most complete description of photon migration in turbid media is provided by Time Domain (TD) optical methods which have previously been used to decouple the attenuation coefficient, given from CW intensity measurements, into the underlying absorption and scattering coefficients. However TD methods have not been applied to obtain depth and concentration of fluorophores.

SUMMARY OF THE INVENTION

The invention relates to the measurement of fluorophores localization and concentration within a turbid medium. More specifically the invention relates to the measurement of fluorophores depth and concentration within a turbid medium.

There is advantageously provided a method wherein TD optical methods are used to decouple fluorophore depth and concentration from a single source and detector measurement employing a direct analysis technique, thereby avoiding the aforementioned burden of CW tomography and overcoming the limitations of conventional CW direct fluorescence intensity imaging.

In one embodiment there is provided method for determining the depth of a volume comprising a fluorophore in a turbid medium using time domain (TD) optical fluorescence by obtaining Temporal Point Spread Function (TPSF) data, by injecting light at an injection point on an object at an excitation wavelength of the fluorophore and detecting light at a detection point of the object at an emission wavelength of the fluorophore, determining a time ($t_{max}$) substantially corresponding to the maximum of the TPSF and correlating $t_{max}$ with the depth. In a preferred embodiment, the injection and detection points are a back-reflection geometry and are substantially equidistant from the volume comprising the fluorophore. In this case, the depth may be expressed as a function of the speed of light in the medium, the scatter coefficient in the medium, the lifetime of the fluorophore in the medium and $t_{max}$. Thus, by measuring or providing an estimate of the above parameters, the depth of fluorophore can be estimated.

In another embodiment there is also provided a method for estimating the concentration of a fluorophore in a volume of a turbid medium using optical fluorescence by obtaining the depth of the volume comprising the fluorophore, providing optical properties for the medium, obtaining a intensity surface reflection measurement of the fluorophore, and normalizing the CW intensity measurements using optical properties of the medium and the fluorophore depth to obtain a relative fluorophore concentration. An absolute concentration may also be obtained by calibrating the fluorescence emission using known concentrations of the fluorophores embedded in the medium.

In yet a further embodiment there is provided a method for generating a tomographic image of a fluorophore distribution in a turbid medium by obtaining a topographic image of the fluorophore distribution, determining the depth of a plurality of volumes of interest comprising the fluorophore using depth determination methods of the present invention, and combining the depth information and the topographic image to generate a tomographic image of the fluorophore distribution.

In another aspect of the invention there is provided an apparatus for determining the concentration of a fluorophore in a turbid medium which comprises a light source, optically coupled to a source channel and the object, to inject light in said object at a desired point and excitation wavelength; a first detector channel, optically coupled to a photon detector and the object, in a back-reflection geometry relative to the source channel, to acquire at least one TPSF from a desired point on the object to determine the depth of the fluorophore, a second detector channel in a trans-illumination geometry relative to the source channel, to measure an emission intensity of the fluorophore, a means for spatially positioning the object relative to the channels, a depth calculator and a concentration calculator.

BRIEF DESCRIPTION OF THE DRAWINGS

Further features and advantages of the present invention will become apparent from the following detailed description, taken in combination with the appended drawings, in which:

FIG. 4A is a schematic representation of the back-reflection geometry;

FIG. 4B is a schematic representation of the trans-illumination geometry;

FIG. 6 is a schematic representation of an example of the apparatus combining the back-reflection and the trans-illumination geometries.

It will be noted that throughout the appended drawings, like features are identified by like reference numerals.

DETAILED DESCRIPTION OF THE PREFERRED EMBODIMENT

The fluorescence emission from a fluorophore embedded in a turbid medium can be measured over time using time domain (TD) optical fluorescence to generate Temporal Point Spread Function (TPSF) data. Acquisition of such data will be described in more details below, but briefly it consists in injecting a pulse of light at an excitation wavelength in the medium comprising the fluorophore and detecting the emission fluorescence as a function of time. TD fluorescence experiments were conducted with a single source-detector measurement for a small inclusion of fixed flurophore concentration submerged into a turbid, liquid medium. It was observed that the temporal position of the maximum of the TPSF generated by the fluorescent photons ($t_{max}$) increased with the depth of the submersion of the inclusion in the turbid medium.

TD fluorescence experiments were also conducted with single source-detector measurements for small inclusions of various fluorophore concentrations submerged at fixed depths in a turbid, liquid medium. It was observed that $t_{max}$ generated by the fluorescent photons remained constant for inclusions of the same submersion depth, regardless of their fluorophore concentration. These results are displayed in FIG. 1 which is a tri-dimensional plot of $t_{max}$ as a function of depth and concentration of the fluorophore. Hence it was demonstrated that the measurement of $t_{max}$ from a fluorophore inclusion allows the determination of the depth of a fluorophore independent of its concentration.

Figure 2:
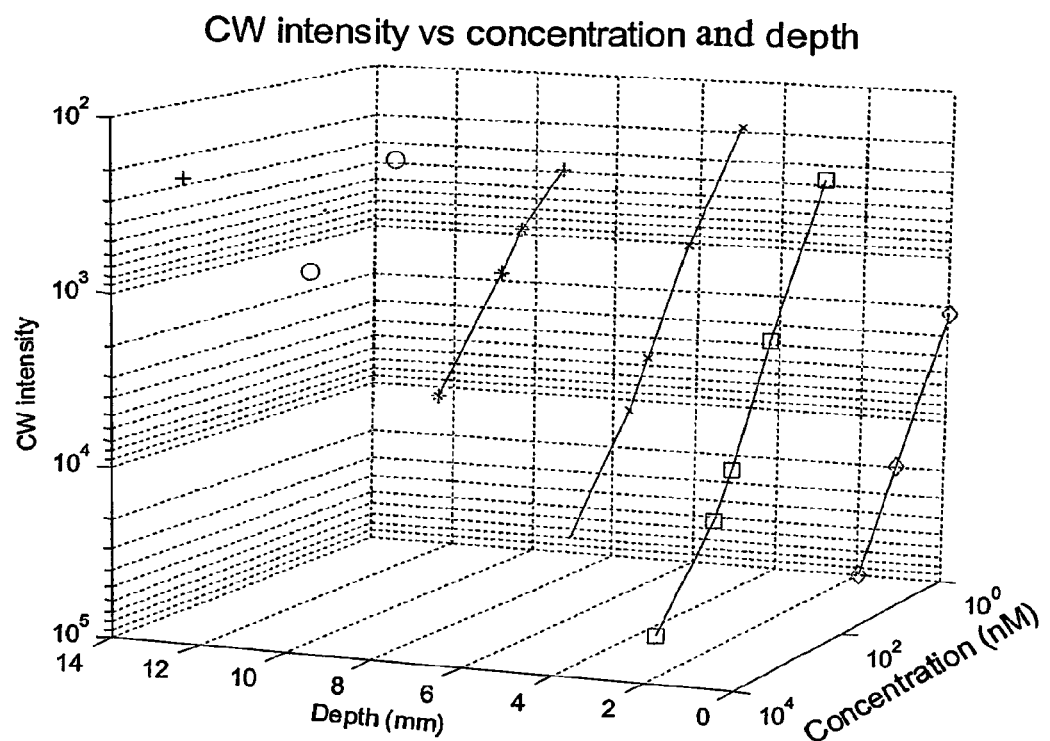
FIG. 2 is a 3-dimensional graphic relating CW signal intensity, depth of fluorophore and the concentration of the fluorophore.

For the above series of experiments, CW data was also generated by temporally integrating the complete TPSF. As expected, the CW fluorescence intensity decreased as the depth of the fixed fluorophore concentration increased, but it also decreased as the fluorophore concentration of inclusions at a fixed depth decreased, as shown in FIG. 2. Hence, it was demonstrated that direct CW fluorescence intensity measurements alone cannot decouple fluorophore inclusion concentration from depth.

In the present description it will be appreciated that the intensity of the fluorescence emission of the fluorophore can be obtained using direct CW measurements or by integrating a Temporal Point Spread Function (TPSF) obtained by the time domain (TD) method. It will be noted that time domain data can be obtained by connecting frequency domain data using Fourier Transform.

It will also be appreciated that the term fluorophore can refer to either an extrinsic fluorophore which is understood to be a fluorophore that is added to a given medium or an intrinsic fluorophore which is understood to be a fluorophore that is normally comprised in a given medium. For example biological tissue may comprise molecules that naturally fluoresce and are therefore intrinsic fluorophores.

In the present description it is also meant by turbid medium, any medium that scatters light. Such media may comprise but are not limited to biological tissues such as breast, brain, muscles and the like. Furthermore, while the embodiments described herein exemplify the application of the method and apparatus to small animals, the method and apparatus can also be applied to larger animals including humans.

Figure 1:
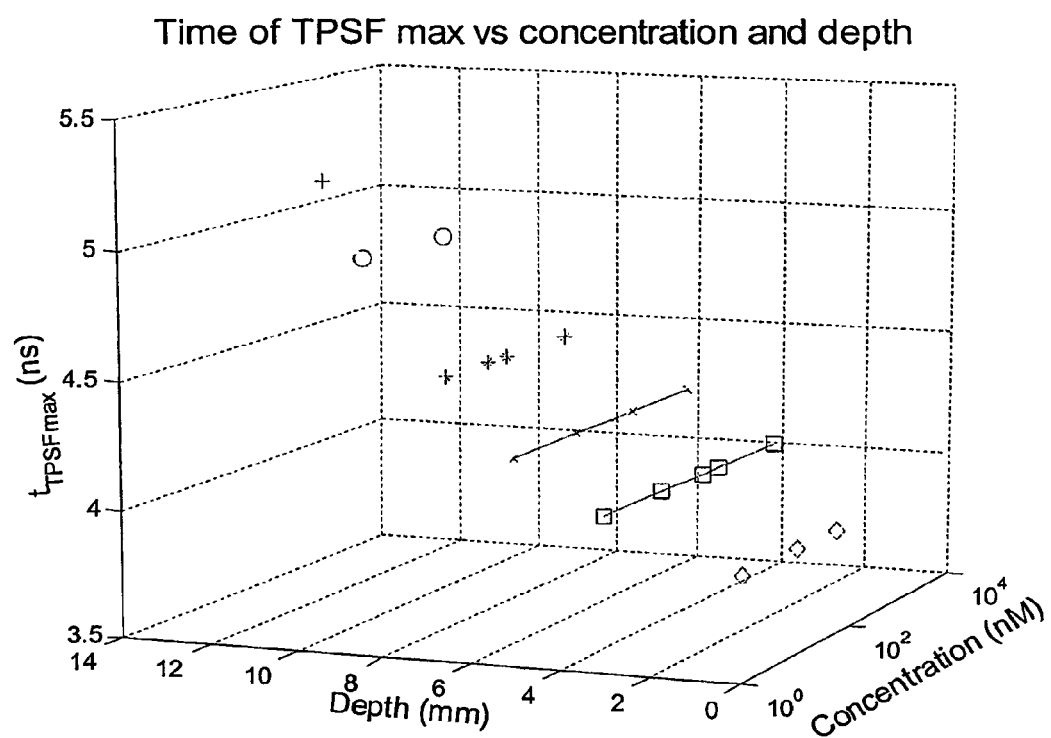
FIG. 1 is a 3-dimensional graphic relating $t_{max}$, depth of fluorophore and the concentration of the fluorophore.

Thus in view of the results shown in FIGS. 1 and 2, the depth, within an object comprising turbid medium, of a volume comprising a fluorophore can be determined by establishing a calibration curve for which $t_{max}$ measurements are obtained for known depth of the volume and using this calibration curve to estimate the depth of a volume comprising a fluorophore which depth is originally unknown.

The depth of more than one fluorophore can be assessed by injecting light of different wavelengths corresponding to the excitation wavelengths of the different fluorophores and detecting light at an emission wavelength for each of the fluorophore.

Under certain assumptions such as assuming that the optical properties of the medium are the same at the excitation and emission wavelength, the fluorescence intensity as a function of time can be expressed by the Born approximation:

$$\phi(t) \cong \sum_{dipoles} \left( QC \frac{r_{sp} + r_{pd}}{4\pi D r_{sp} r_{pd}} v(4\pi D v t)^{-\frac{3}{2}} e^{-\frac{(r_{sp}+r_{pd})^2}{4Dvt} - \mu_a v t} \right) * \left( \frac{e^{\frac{t}{\tau}}}{\tau} \right) * (IR) \quad \text{(equation 1)}$$

Where:

$r_{sp}$ is the distance from source s (point on the object at which light is injected) to fluorophore depth position p;

$r_{pd}$ is the distance from fluorophore depth position p to detector d;

$\mu_a$ is the optical absorption coefficient;

D is the optical diffusion coefficient, $$D = \frac{1}{3\mu_s'}$$

where; $\mu_s'$ is the reduced optical scatter coefficient;

v is the speed of light in the medium;

Q is the quantum efficiency;

C is the concentration of the fluorophore;

$\tau$ is the lifetime of the fluorophore; and

IR is the impulse response of the instrument used to measure fluorescence

By setting the first derivative of equation 1 as a function of time equal to zero, the time position of the maximum of the TPSF ($t_{max}$) can be found. Under certain approximations (absorption is small at time shorter than $t_{max}$, the scatter coefficient is known or can be approximated) and by assuming that $r_{sp}$ is approximately equal to $r_{pd}$, it is found that the following equation can be derived from equation 1:

$$t_{max} \cong \frac{d\sqrt{\tau}}{\sqrt{Dv}} \quad \text{(equation 2)}$$

where d is the depth of the volume comprising the fluorophore.

Figure 3:
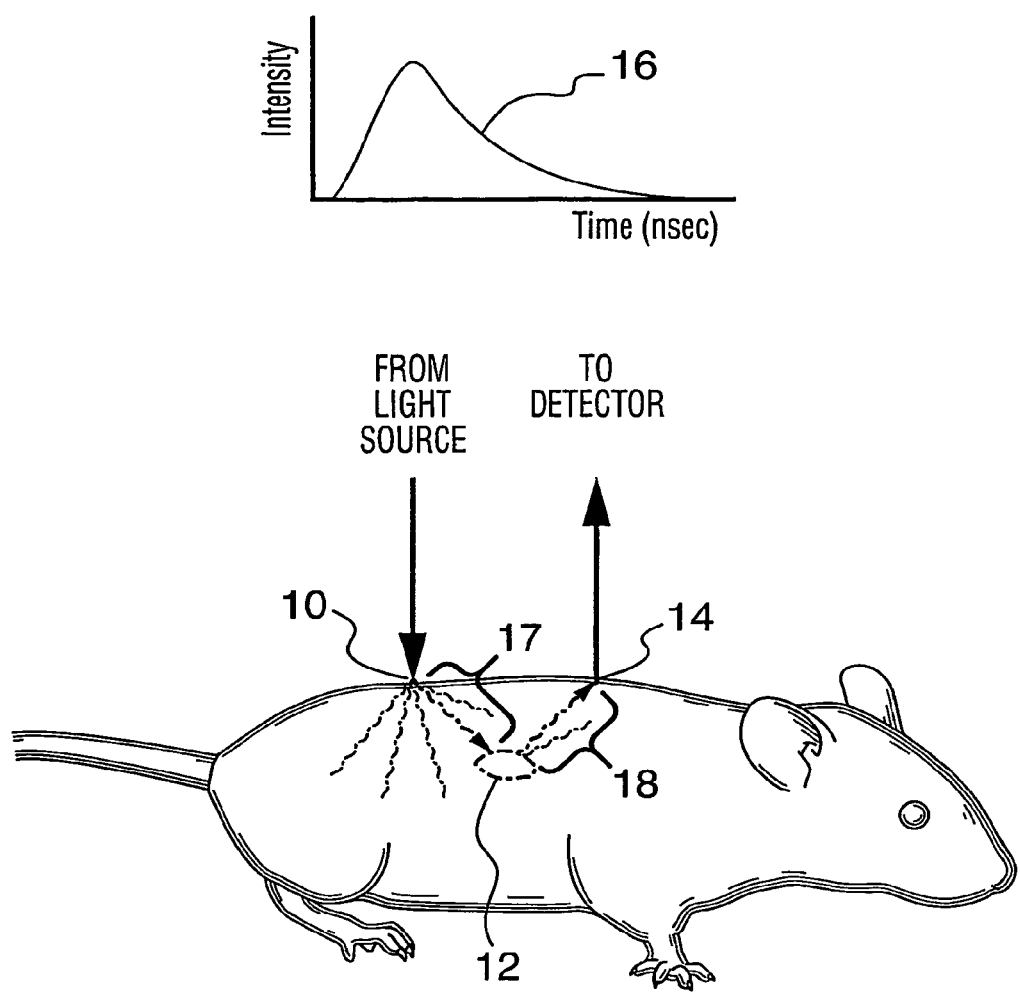
FIG. 3 is a schematic representation of a preferred fluorescence signal acquisition configuration for depth determination.

FIG. 3 schematically depicts how the TPSF may be acquired. One of more pulse of light at an excitation wavelength is injected at injection point 10 in an object (in this case exemplified by a mouse) comprising one or more fluorophore. The photons diffuse within the tissue and a certain fraction of the photons eventually reach the fluorophore molecules contained in a volume of interest (VOI) 12 which are thereby excited. The molecules then emit a fluorescence signal. The emission photons will diffuse and a fraction of them will reach detection point 14 to produce TPSF data 16. In a preferred embodiment the acquisition of the fluorescence signal is performed in the back-reflection mode as shown in FIG. 3, with the injection and detection points substantially equidistant from the volume comprising the fluorophore. That is $r_{sp}$ 17 and $r_{pd}$ 18 are approximately equal.

As can be seen from equation 2, the depth of the fluorophore is proportional to $t_{max}$ but also to the speed of light, the scatter coefficient and the lifetime of the fluorophore. In order to determine the depth of a volume comprising a fluorophore in a turbid medium, the speed of light, scatter coefficient and lifetime can be provided using known values for the medium. Alternatively, the scattering coefficient and lifetime can be provided using the standard time domain approach by direct measurements.

The scattering coefficient can be determined at either the excitation and/or emission wavelengths of the fluorophore, since in a preferred embodiment the method assumes that these values are the same for the excitation and emission wavelengths. However, it is also possible to derive $t_{max}$ by using the scattering coefficient as determined at both the excitation and emission wavelengths of the fluorophore. In this respect, it will be appreciated that a more general form of equation 1 in which the absorption and scatter coefficients, determined at both the emission and excitation wavelengths, are used is also encompassed in the present invention.

The calculation from which equation 2 is derived is based in part on the assumption that the distance between the point of light injection 10 at the surface of the object and volume 12 and between volume 12 and the point of fluorescence emission detection 14 is substantially identical. Determination of the injection and detection points relative to the volume of interest in the reflection geometry can be achieved, for example by obtaining a topographic image of the fluorophore in a region of interest. While the topographic image can be acquired using the system of the present invention, it can also be acquired by systems and methods that are well known in the art (see for example WO 2004/044562 and U.S. Pat. No. 6,217,847). In this respect the 2D (topographic) image may be obtained by optical modalities such as TD, CW and frequency domain (FD).

The injection and detection points may also be determined based on prior knowledge of the expected location of the fluorophore in a plane substantially perpendicular to the depth. For example, the location of the fluorophore may be known and this information may be used to select the injection and detection points.

Once the injection and detection points have been determined, TPSF data is then acquired by injecting pulses of light at an excitation wavelength of the fluorophore at the injection point and by detecting as a function of time the fluorescence emission at an emission wavelength. The time at which the TPSF reaches a maximum ($t_{max}$) is then recorded and used in the above relationships (either equation 1 or equation 2) to determine the depth of the fluorophore.

It will be appreciated that a single injection/detection points pair is sufficient to determine the depth, therefore providing a rapid method for determination of depth. However, it is also possible to use multiple injection/detection pairs to improve the accuracy of depth determination.

For a given depth, the intensity I of the emission signal detected at the surface can be related to fluorophore concentration by the optical properties of the medium (absorption and scattering coefficients) and the depth of the fluorophore.

$$I \propto Ce^{-\sqrt{\frac{\mu_a}{D}} d} \quad \text{(equation 3)}$$

Using time-domain information as described above, the depth d can be determined. Isolating C in equation 3 and knowing signal intensity and depth of the fluorophore, one can thus recover the concentration of fluorophore (i.e. the amount of fluorescent molecules per unit volume) within an accuracy that depends exponentially on the recovered depth accuracy. Thus, in another aspect of the invention, estimates of the relative concentration of the fluorophore, $Conc._{Relative}$, can be obtained by determining its depth, d, and normalizing the surface intensity measurement, I, as follows (Equation 4):

$$Conc._{Relative} = Id^2 e^{2d\sqrt{\mu_a/D}} \quad \text{(equation 4)}$$

under certain assumptions, Equation 4 can be derived from equation 1.

Determination of the concentration may also be derived from equation 1. Referring to FIG. 4a, it can be seen that, when measurements are performed in a back-reflection geometry, the distances $r_{sp}$ 17 and $r_{pd}$ 18 depend on the depth d of the fluorophore. Since there is a certain variation associated with the measurement of the depth determination, the determination of the concentration will carry the variation associated with depth determination. Therefore, in a preferred embodiment, the intensity I may be acquired in the trans-illumination mode as shown in FIG. 4B, whereby the distance between the point of injection 10 and the point of detection 15 is constant for a given object and is equal to $r_{sp}+r_{pd}$. Thus, in the trans-illumination mode the term "$r_{sp}+r_{pd}$" does not depend on d. It is therefore possible to obtain a better estimation of the concentration.

In a further embodiment of the invention there is therefore provided a method for determining the concentration of a fluorophore comprising obtaining the depth of the fluorophore using a back-reflection geometry as described above and a fluorescence intensity measurement in a trans-illumination geometry and calculating the concentration based on the measured depth.

This method provides a means for rapidly comparing the relative concentration of a fluorophore at two or more distinct locations. The determination of the relative concentration of a fluorescently labeled antibody in different organs of an animal provides a non-limiting example.

Relative concentration can be further processed to estimates of absolute concentration if the surface intensity measurement is absolutely calibrated. That is to say a calibration curve can be established for I using known concentrations of the fluorophore. The scattering and absorption coefficients can be provided using known values for the medium or alternatively may be provided using the standard time domain approach by direct measurements. Biological tissues may not conveniently allow for easy calibration since incorporating known concentrations of fluorophores may be difficult. In these cases, the calibration may be effected in a turbid medium having similar optical properties as the biological tissue to be measured.

By further analyzing the fluorescence intensity data from the above experiments (FIGS. 1 and 2), it was possible to calibrate the optical attenuation of the turbid medium. In other words, for the inclusion of fixed fluorophore concentration, the optical attenuation can be obtained by fitting the decrease of fluorescence intensity measured by the surface detector as the inclusion depth increases. The same optical attenuation can then be used to describe the decrease of fluorescence intensity of fluorophore with other concentrations as the inclusion depth increases.

Given the above series of experiment, the inclusion may be submerged at unknown depth and concentration in the turbid medium. As stated above, direct fluorescence intensity measurements alone cannot decouple the inclusion depth from its fluorophore concentration. However TD experiments can provide $t_{max}$ which yields the inclusion depth. Once the inclusion depth is known, the calibrated optical attenuation of the turbid medium can be used to normalize the fluorescence intensity measurement to yield the relative concentration of the fluorophore inclusion. Further, an absolute calibration of the intensity measurements permits estimates of the absolute concentration.

In yet a further embodiment of the invention there is provided a method for generating a tomographic image of a fluorophore distribution. Topographic images of a region of interest can be obtained using well known method such as CW, TD frequency domain (FD) optical imaging. Such topographic images can be combined with the depth and/or concentration information obtained by the methods described above to generate a 3-dimension (tomographic) image of a volume of interest comprising one or more fluorophores.

It will also be appreciated that the surface intensity may be provided by temporarily integrating the time domain fluorescent measurement.

Figure 5:
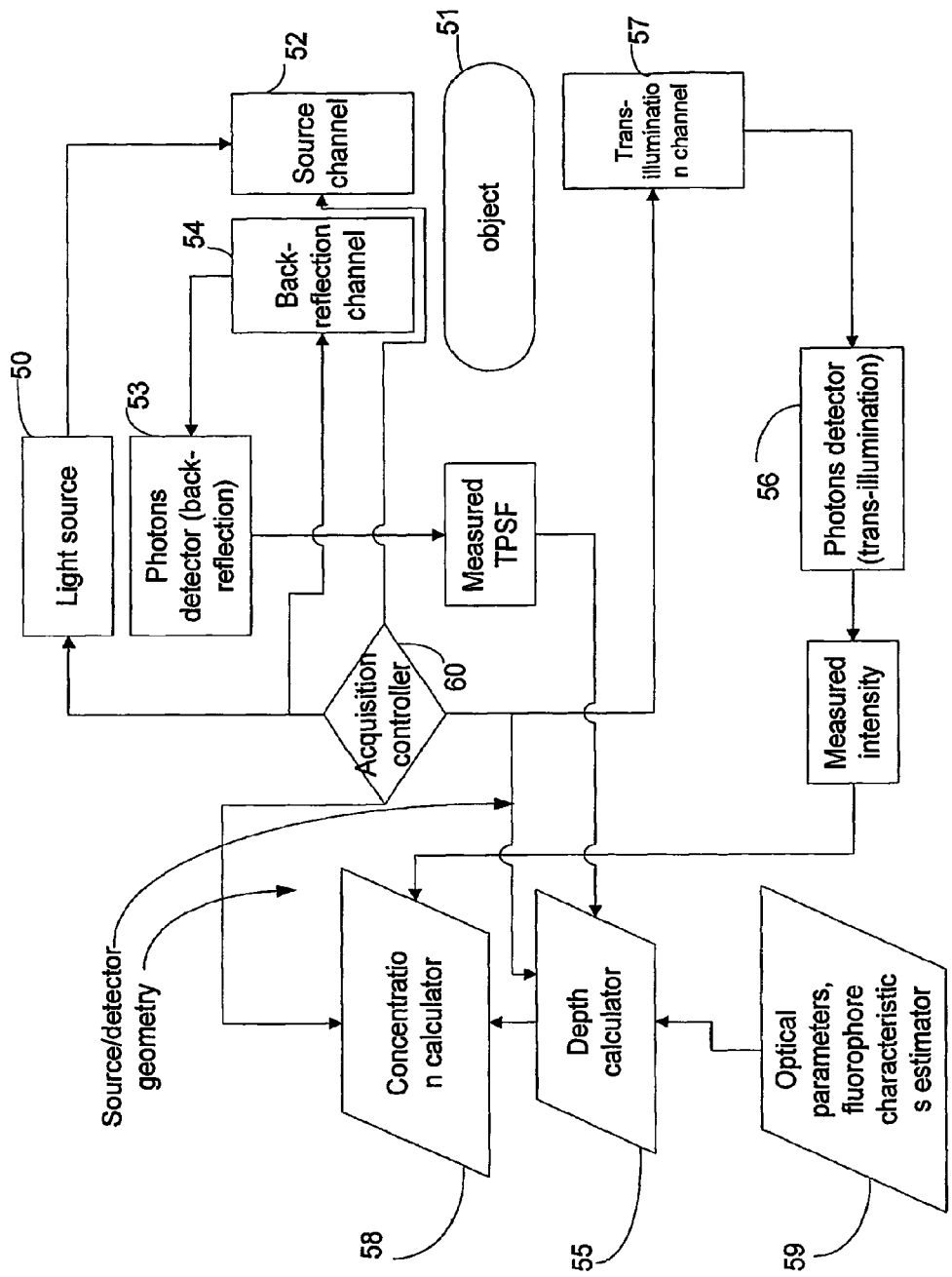
FIG. 5 is a schematic representation of an example of the system combining the back-reflection and the trans-illumination geometries.

With reference to FIG. 5, an example of the system of the present invention for measuring fluorophore concentration is schematically illustrated. Light source 50 is optically coupled to object 51, which comprises the fluorophore, through source channel 52. Light emitted by the fluorophore is optically coupled to photons detector 53 through back-reflection channel 54. When operated in the TD mode, the measured TPSF can be acquired and used by depth calculator 55 to determine the depth of the fluorophore. The intensity of the fluorescence signal can be measured either simultaneously with the TPSF or sequentially by detecting photons with photons detector 56 optically coupled to the object through trans-illumination channel 57. The measured intensity is then combined with the calculated depth to calculate the concentration at concentration calculator 58. Calculation of the depth can be performed with equation 2 which requires estimation of scatter coefficient, speed of light in medium, and lifetime of fluorophore which are provided by estimator 59.

Acquisition controller 60 controls source/detector geometry and source characteristics such as intensity, pulse length, wavelengths and the like.

A schematic diagram of an embodiment of the apparatus is shown in FIG. 6. Source 61 provides light at the excitation wavelength of a fluorophore embedded in object 62. The light is directed towards a predetermined point of light injection on object 62 using source channel 64. The source channel is an optical means for directing the excitation light to the desired point on the object and may consist of a fiber optic, reflective mirrors and the like. A first detector channel 65 is positioned to detect emission light in a back-reflection geometry and a second detector channel 66 is position in a trans-illumination geometry. The detector channels are optical means for collecting the emission light from desired points on object 62 and are optically coupled to photon detection 69. As for the source channel, the detector channels may consist of a fiber optic, reflective mirrors and the like. The source and detector channels may operate in a contact or free space optic configuration. By contact configuration it is meant that one or more of the components of the source and/or detector channel is in contact with object 62. By free space optic it is meant that light is propagated through air and directed to or collected from the desired points with appropriate optic components. An example of a free space optic system is described in WO 2004/044562. The detector channels can be coupled to spectral filters 67 to selectively detect an emission wavelength of the fluorophore.

The source and detector channels can be physically mounted on a common gantry 68 so as to maintain them in a fixed relative position. In such an arrangement, the position of the point of injection of excitation light and that of the point from which the emission light is collected can be selected by moving (scanning) the gantry relative to the object. Alternatively relative positioning of the object and the source/detector channels may be accomplished by moving the object relative to the gantry.

The position of the source and detector channels may also be controlled independently from one another. It will be appreciated that the position of the back-reflection and trans-illumination detector channels can also be independently controlled. Furthermore the system may also allow a combination of arrangements. For example, the trans-illumination channel may be in a fixed position relative to the source channel whereas the position of the back reflection channel is controlled independently. The favored arrangement may depend on the type of object being probed, the nature and/or distribution of the fluorophore and the like. In a preferred embodiment, the source channel and detector channel are co-axially positioned.

While the back-reflection detection is preferably done in the time-domain to provide depth information, the intensity of the fluorescence in the trans-illumination geometry may be detected by either CW, TD or FD domain modality.

Figure 7:
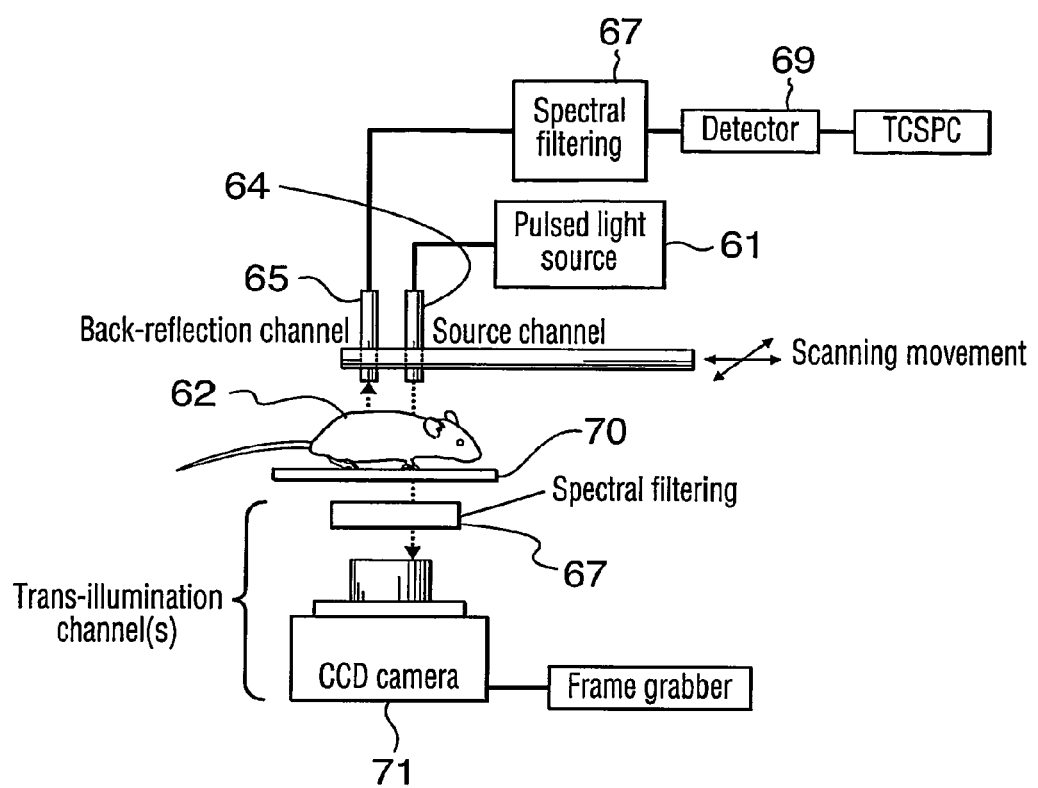
FIG. 7 is a schematic representation of an example of the apparatus combining the back-reflection and trans-illumination geometries wherein the trans-illumination detector channel is a CCD camera.

Detectors for the emitted light in the time domain may comprise time correlated single photon counting devices (TCSPC), time gated intensified charged couple device (ICCD) and the like. For continuous wave measurements photon multipliers, CCD cameras and the like may be used. The detector channel in the trans-illumination geometry may comprise a CCD camera 71 as show in FIG. 7.

The object can be placed on a transparent platform 70 or can be suspended in the desired orientation by providing attachment means that can be removeably secured to the object and an appropriate structure within the apparatus. Preferably the position of the platform or the attachment means can be adjusted along all three spatial coordinates.

In the trans-illumination geometry the thickness of the object is preferably determined to provide a value for the optical path $(r_{sp}+r_{pd})$. If the channels are in a contact configuration the thickness may be provided by the distance between the source channel at the point of light injection and the trans-illumination detector channel at the point of light collection. In the case of a free space optic configuration the thickness may advantageously be provided by a profilometer which can accurately determine the coordinates of the contour of the object.

A plurality of fluorophores can be monitored simultaneously by providing appropriate excitation and emission wavelengths. To this end source 61 may consist of a plurality of sources operating at different wavelengths. Alternatively the source may be a broadband source optically coupled to a spectral filter to select appropriate wavelengths. The emission wavelengths can be de-multiplexed into individual wavelengths by spectral filter 69. Selection of wavelength may also be effected using other appropriate optical components such as prisons.

As described above the depth of the fluorophore may be determined by measuring $t_{max}$ from a TPSF obtained from time-domain measurements. Furthermore the concentration of the fluorophore is advantageously measured using a trans-illumination geometry. In a preferred embodiment, the apparatus of the present invention provides for the simultaneous measurement of the depth, using a back-reflection geometry, and the concentration using a trans-illumination geometry. Advantageously, this simultaneous determination can be achieved with a single source of light, and the positioning of the source channel can be coordinated with the positioning of the back-reflection and the trans-illumination detectors.

It will be appreciated that multiple source and detector channels can be provided for simultaneous or sequential multiple measurements.

The embodiment(s) of the invention described above is(are) intended to be exemplary only. The scope of the invention is therefore intended to be limited solely by the scope of the appended claims.

We claim:

1. A method for determining depth of a volume comprising a fluorophore in a turbid medium using time domain (TD) optical fluorescence, said method comprising:
    i) obtaining at least one temporal point spread function (TPSF) by injecting light at an injection point at an excitation wavelength of said fluorophore and detecting light at a detection point at an emission wavelength of said fluorophore;
    ii) determining a time $t_{max}$ substantially corresponding to the maximum of said TPSF;
    iii) correlating said $t_{max}$ with said depth to determine the depth, and wherein said depth is insensitive to fluorophore concentration.

2. The method as claimed in claim 1 wherein said step of correlating comprises:
    a) establishing a calibration curve of $t_{max}$ as a function of depth for a plurality of depths;
    b) using said calibration curve and said $t_{max}$ determined in step ii) to obtain said depth of said volume.

3. The method as claimed in claim 1 wherein said injection and detection points are in a backreflection geometry.

4. The method as claimed in claim 3 wherein said injection and detection points are substantially equidistant from said volume.

5. The method as claimed in claim 4 wherein said step of correlating comprises:
    a) providing scatter coefficient, speed of light in said medium and a lifetime of said fluorophore in said medium;
    b) calculating said depth using said $t_{max}$ and said scatter coefficient, said speed of light and said lifetime.

6. The method as claimed in claim 5 further comprising a step of estimating a position of said fluorophore in a plane substantially perpendicular to said depth prior to said step of obtaining said TPSF.

7. The method as claimed in claim 6 wherein said step of estimating is performed by obtaining a topographic image of a region of interest containing said fluorophore.

8. The method as claimed in claim 5 wherein said scatter coefficient and lifetime are obtained using time domain optical measurements of said medium.

9. The method as claimed in claim 5 wherein said scatter coefficient, lifetime and speed of light are obtained by matching said medium with a similar medium in a database for which optical properties are known.

10. The method as claimed in claim 5, wherein said scatter coefficient and said speed of light are substantially the same at both the excitation or emission wavelength of the fluorophore and are determined at either said emission or said excitation wavelength.

11. The method as claimed in claim 5, wherein said scatter coefficient and said speed of light are determined at the fluorophore excitation and emission wavelength.

12. The method as claimed in claim 1 wherein said fluorophore is an intrinsic or extrinsic fluorophore.

13. A method for estimating concentration of a fluorophore in a volume in a turbid medium using optical fluorescence, said method comprising:
    i) obtaining depth of said volume using the method of claim 1;
    ii) obtaining a fluorescence emission Intensity of said fluorophore; and
    iii) deriving said concentration from a fluorescence emission equation.

14. The method as claimed in claim 13 wherein said emission intensity is obtained in a back-reflection configuration.

15. The method as claimed in claim 14 wherein said emission intensity is obtained in a modality selected from time domain, frequency domain and continuous wave.

16. The method as claimed in claim 13 wherein said fluorescence emission intensity is obtained in a trans-illumination configuration.

17. The method as claimed in claim 16 wherein said emission intensity is obtained in a modality selected from time domain, frequency domain and continuous wave.

18. The method as claimed in claim 13 wherein said equation provides concentration of a fluorophore as a function of depth, scatter coefficient and absorption coefficient.

19. The method as claimed in claim 18 wherein said coefficients are obtained using time domain optical measurements of said medium.

20. The method as claimed in claim 18 wherein said coefficients are obtained by matching said medium with a similar medium from a database for which the optical properties are known.

21. The method as claimed in claim 18, wherein said coefficients are substantially the same at both the excitation or emission wavelength of the fluorophore and is determined at either said emission or said excitation wavelength.

22. The method as claimed in claim 18, wherein said at least one optical property is determined at the fluorophore excitation and emission wavelength.

23. The method as claimed in claim 13 wherein said concentration is a relative concentration.

24. The method as claimed in claim 13 wherein said concentration is an absolute concentration derived by calibrating said intensity.

25. A method for generating a tomographic image of a fluorophore distribution in a turbid medium said method comprising:
   i) obtaining a topographic image of said fluorophore distribution;
   ii) determining depth of a plurality of volumes of interest comprising said fluorophore using the method as claimed in claim 1;
   iii) combining said depth information and said topographic image to generate a tomographic image of said distribution.

26. The method as claimed in claim 25 wherein said tomographic image is further processed with the method as claimed in claim 13 to generate a tomographic flurorophore concentration image.

27. A method for determining a relative or absolute concentration of a fluorophore in a turbid medium said method comprising:
   i) establishing a calibration curve relating an emission intensity measurement in said turbid medium and concentration and depth of said fluorophore;
   ii) determining a depth of said fluorophore using the method as claimed in claim 1; and
   iii) determining said concentration using said calibration curve.

28. The method as claimed in claim 1 wherein time domain information is obtained by acquiring Frequency Domain (FD) data and applying a Fourier Transform to said data.

* * * * *